US011420077B2

(12) United States Patent
Ramezanzadeh Moghadam et al.

(10) Patent No.: US 11,420,077 B2
(45) Date of Patent: Aug. 23, 2022

(54) RADIATION DETECTOR CALIBRATION

(71) Applicant: Sun Nuclear Corporation, Melbourne, FL (US)

(72) Inventors: Amir Ramezanzadeh Moghadam, Melbourne, FL (US); Jakub Kozelka, Melbourne, FL (US)

(73) Assignee: SUN NUCLEAR CORPORATION, Melbourne, FL (US)

( * ) Notice: Subject to any disclaimer, the term of this patent is extended or adjusted under 35 U.S.C. 154(b) by 58 days.

(21) Appl. No.: 17/134,907

(22) Filed: Dec. 28, 2020

(65) Prior Publication Data

US 2021/0113858 A1 Apr. 22, 2021

Related U.S. Application Data

(63) Continuation of application No. 16/846,227, filed on Apr. 10, 2020, now Pat. No. 10,881,880, which is a continuation of application No. 14/694,865, filed on Apr. 23, 2015, now Pat. No. 10,617,891.

(51) Int. Cl.
*A61N 5/10* (2006.01)
*A61B 5/055* (2006.01)

(52) U.S. Cl.
CPC ............ *A61N 5/1075* (2013.01); *A61B 5/055* (2013.01); *A61N 5/1049* (2013.01); *A61N 5/1045* (2013.01); *A61N 5/1071* (2013.01); *A61N 2005/1054* (2013.01)

(58) Field of Classification Search
None
See application file for complete search history.

(56) References Cited

U.S. PATENT DOCUMENTS

| | | | |
|---|---|---|---|
| 759,608 A | 5/1904 | Harper |
| 1,239,145 A | 9/1917 | Wantz |
| 2,818,510 A | 12/1957 | Verse |
| 3,033,985 A | 5/1962 | Petree |
| 3,267,728 A | 8/1966 | Solomons |
| 3,327,213 A | 6/1967 | Wald, Jr. |
| 3,394,258 A | 7/1968 | Schleiger |
| 3,433,953 A | 3/1969 | Sweet |

(Continued)

FOREIGN PATENT DOCUMENTS

| CA | 2718408 | 9/2009 |
|---|---|---|
| DE | 102009039345 A1 | 3/2011 |

(Continued)

OTHER PUBLICATIONS

"HI-ART"; www.tomotherapy.com; TomoTherapy, Madison, WI; 2007; pp. 1-8.

(Continued)

*Primary Examiner* — Hoon K Song
(74) *Attorney, Agent, or Firm* — Pillsbury Winthrop Shaw Pittman LLP (57) ABSTRACT

A computer program product, method, system and device that acquires, by a radiation detector, exit radiation measurement information during delivery of patient treatment. Patient anatomy information is also received and a radiation detector response calibration is determined utilizing at least the exit radiation measurement information, the patient anatomy information, and at least a portion of a radiation treatment plan.

16 Claims, 5 Drawing Sheets

(56) References Cited

U.S. PATENT DOCUMENTS

| | | |
|---|---|---|
| 3,665,762 A | 5/1972 | Domen |
| 3,783,251 A | 1/1974 | Pavkovich |
| 3,790,794 A | 2/1974 | Murray |
| 3,980,885 A | 9/1976 | Steward |
| 4,058,832 A | 11/1977 | Vagi |
| 4,063,097 A | 12/1977 | Barrett |
| 4,107,531 A | 8/1978 | Garratt |
| 4,157,472 A | 6/1979 | Barrett |
| 4,312,224 A | 1/1982 | Domen |
| 4,450,440 A | 5/1984 | White |
| 4,455,609 A | 6/1984 | Inamura |
| 4,613,754 A | 9/1986 | Vinegar |
| 4,729,099 A | 3/1988 | Iverson |
| 4,765,749 A | 8/1988 | Bourgade |
| 4,777,442 A | 10/1988 | Rosenthal |
| 4,887,287 A | 12/1989 | Cobben |
| 5,099,505 A | 3/1992 | Seppi |
| 5,160,337 A | 11/1992 | Cosman |
| 5,262,649 A | 11/1993 | Antonuk |
| 5,388,142 A | 2/1995 | Morris |
| 5,394,452 A | 2/1995 | Swerdloff |
| 5,596,653 A | 1/1997 | Kurokawa |
| 5,602,892 A | 2/1997 | Llacer |
| 5,621,214 A | 4/1997 | Sofield |
| 5,622,187 A | 4/1997 | Carol |
| 5,627,367 A | 5/1997 | Sofield |
| 5,635,709 A | 6/1997 | Sliski |
| 5,640,436 A | 6/1997 | Kawai |
| 5,661,310 A | 8/1997 | Jones |
| 5,704,890 A | 1/1998 | Bliss |
| 5,712,482 A | 1/1998 | Gaiser |
| 5,873,826 A | 2/1999 | Gono |
| 5,988,875 A | 11/1999 | Gershfeld |
| 6,038,283 A | 3/2000 | Carol |
| 6,125,335 A | 9/2000 | Simon |
| 6,131,690 A | 10/2000 | Galando |
| 6,148,272 A | 11/2000 | Bergstrom |
| 6,175,761 B1 | 1/2001 | Frandsen |
| 6,207,952 B1 | 3/2001 | Kan |
| 6,257,552 B1 | 7/2001 | Crow |
| 6,261,219 B1 | 7/2001 | Meloul |
| 6,301,329 B1 | 10/2001 | Surridge |
| 6,322,249 B1 | 11/2001 | Wofford |
| 6,345,114 B1 | 2/2002 | Mackie |
| 6,364,529 B1 | 4/2002 | Dawson |
| 6,398,710 B1 | 6/2002 | Ishikawa |
| 6,516,046 B1 | 2/2003 | Froehlich |
| 6,535,574 B1 | 3/2003 | Collins |
| 6,535,756 B1 | 3/2003 | Simon |
| 6,552,347 B1 | 4/2003 | Dimcovski |
| 6,560,311 B1 | 5/2003 | Shepard |
| 6,594,336 B2 | 7/2003 | Nishizawa |
| 6,609,626 B2 | 8/2003 | Young |
| 6,609,826 B1 | 8/2003 | Fujii |
| 6,626,569 B2 | 9/2003 | Reinstein |
| 6,636,622 B2 | 10/2003 | Mackie |
| 6,648,503 B2 | 11/2003 | Tanaka |
| 6,712,508 B2 | 3/2004 | Nilsson |
| 6,788,759 B2 | 9/2004 | Op De Beek |
| 6,799,068 B1 | 9/2004 | Hartmann |
| 6,810,107 B2 | 10/2004 | Steinberg |
| 6,810,108 B2 | 10/2004 | Clark |
| 6,833,707 B1 | 12/2004 | Dahn |
| 6,839,404 B2 | 1/2005 | Clark |
| 6,853,702 B2 | 2/2005 | Renner |
| 6,888,919 B2 | 5/2005 | Graf |
| 6,904,119 B2 | 6/2005 | Oikawa |
| 6,904,125 B2 | 6/2005 | Van Dyk |
| 6,904,162 B2 | 6/2005 | Robar |
| 6,974,254 B2 | 12/2005 | Paliwal |
| 6,990,368 B2 | 1/2006 | Simon |
| 6,992,309 B1 | 1/2006 | Petry |
| 7,016,454 B2 | 3/2006 | Warnberg |
| 7,065,812 B2 | 6/2006 | Newkirk |
| 7,076,023 B2 | 7/2006 | Ghelmansarai |
| 7,098,463 B2 | 8/2006 | Adamovics |
| 7,116,749 B2 | 10/2006 | Besson |
| 7,125,163 B2 | 10/2006 | Eigler |
| 7,127,028 B2 | 10/2006 | Sendai |
| 7,127,030 B2 | 10/2006 | Tamegai |
| 7,142,634 B2 | 11/2006 | Engler |
| 7,193,220 B1 | 3/2007 | Navarro |
| 7,221,733 B1 | 5/2007 | Takai |
| 7,233,688 B2 | 6/2007 | Ritt |
| 7,234,355 B2 | 6/2007 | Dewangan |
| 7,298,820 B2 | 11/2007 | Nelson |
| 7,339,159 B2 | 3/2008 | Juh |
| 7,349,523 B2 | 3/2008 | Jenkins |
| 7,352,840 B1 | 4/2008 | Nagarkar |
| 7,371,007 B2 | 5/2008 | Nilsson |
| 7,386,089 B2 | 6/2008 | Endo |
| 7,420,160 B2 | 9/2008 | Delaperriere |
| 7,453,976 B1 | 11/2008 | Yin |
| 7,455,449 B2 | 11/2008 | Nishimura |
| 7,471,765 B2 | 12/2008 | Jaffray |
| 7,515,681 B2 | 4/2009 | Ebstein |
| 7,579,608 B2 | 8/2009 | Takahashi |
| 7,605,365 B2 | 10/2009 | Chen |
| 7,636,419 B1 | 12/2009 | Nelson |
| 7,668,292 B1 | 2/2010 | Bose |
| 7,734,010 B2 | 6/2010 | Otto |
| 7,750,311 B2 | 7/2010 | Daghighian |
| 7,766,903 B2 | 8/2010 | Blumenkranz |
| 7,773,723 B2 | 8/2010 | Nord |
| 7,778,383 B2 | 8/2010 | Koehler |
| 7,778,392 B1 | 8/2010 | Berman |
| 7,778,680 B2 | 8/2010 | Goode, Jr. |
| 7,782,998 B2 | 8/2010 | Langan |
| 7,945,022 B2 | 5/2011 | Nelms |
| 8,044,359 B2 | 10/2011 | Simon |
| 8,093,549 B2 | 1/2012 | Navarro |
| 8,130,905 B1 | 3/2012 | Nelms |
| 8,136,773 B2 | 3/2012 | Schmutzer |
| 8,147,139 B2 | 4/2012 | Papaioannou |
| 8,218,718 B1 | 7/2012 | Van Herk |
| 8,235,530 B2 | 8/2012 | Maad |
| 8,242,458 B2 | 8/2012 | Rinecker |
| 8,321,179 B2 | 11/2012 | Simon |
| 8,325,878 B2 | 12/2012 | McNutt |
| 8,430,564 B2 | 4/2013 | Simmons |
| 8,457,713 B2 | 6/2013 | Kagermeier |
| 8,474,794 B2 | 7/2013 | Liljedahl |
| 8,536,547 B2 | 9/2013 | Maurer |
| 8,541,756 B1 | 9/2013 | Treas |
| 8,605,857 B1 | 12/2013 | Renner |
| 8,632,448 B1 | 1/2014 | Schulte |
| 8,726,814 B1 | 5/2014 | Matteo |
| 8,794,899 B2 | 8/2014 | Cozza |
| 8,833,709 B2 | 9/2014 | Weng |
| 8,840,304 B2 | 9/2014 | Perez Zarate |
| 8,840,340 B2 | 9/2014 | Eisenhower |
| 8,874,385 B2 | 10/2014 | Takayanagi |
| 8,927,921 B1 | 1/2015 | Nelms |
| 9,050,460 B2 | 6/2015 | Hildreth |
| 9,097,384 B1 | 8/2015 | Simon |
| 9,310,263 B2 | 4/2016 | Thoen |
| 9,463,336 B2 | 10/2016 | Nelms |
| 9,480,861 B2 | 11/2016 | Kapatoes |
| 9,561,388 B2 | 2/2017 | Hildreth |
| 9,586,060 B2 | 3/2017 | Seuntjens |
| 9,750,955 B2 | 9/2017 | McNutt |
| 9,895,557 B2 | 2/2018 | Seuntjens |
| 10,755,823 B2 | 8/2020 | Carette |
| 2001/0042841 A1 | 11/2001 | Lyons |
| 2002/0077545 A1 | 6/2002 | Takahashi |
| 2002/0080912 A1 | 6/2002 | Mackie |
| 2003/0043879 A1 | 3/2003 | Tanaka |
| 2003/0043960 A1 | 3/2003 | Op De Beek |
| 2003/0138077 A1 | 7/2003 | Lee |
| 2003/0231740 A1 | 12/2003 | Paliwal |
| 2004/0066880 A1 | 4/2004 | Oikawa |
| 2004/0068182 A1 | 4/2004 | Misra |
| 2004/0096033 A1 | 5/2004 | Seppi |
| 2004/0113094 A1 | 6/2004 | Lyons |

(56) References Cited

U.S. PATENT DOCUMENTS

| | | |
|---|---|---|
| 2004/0120560 A1 | 6/2004 | Robar |
| 2004/0158145 A1 | 8/2004 | Ghelmansarai |
| 2004/0211917 A1 | 10/2004 | Adamovics |
| 2004/0228435 A1 | 11/2004 | Russell |
| 2004/0251419 A1 | 12/2004 | Nelson |
| 2005/0013406 A1 | 1/2005 | Dyk |
| 2005/0077459 A1 | 4/2005 | Engler |
| 2005/0111621 A1 | 5/2005 | Riker |
| 2006/0002519 A1 | 1/2006 | Jenkins |
| 2006/0033044 A1 | 2/2006 | Gentry |
| 2006/0184124 A1 | 8/2006 | Cowan |
| 2006/0203964 A1 | 9/2006 | Nyholm |
| 2006/0203967 A1 | 9/2006 | Nilsson |
| 2006/0266951 A1 | 11/2006 | Fritsch |
| 2007/0041497 A1 | 2/2007 | Schnarr |
| 2007/0041499 A1 | 2/2007 | Lu |
| 2007/0053492 A1 | 3/2007 | Kidani |
| 2007/0071169 A1 | 3/2007 | Yeo |
| 2007/0081629 A1 | 4/2007 | Yin |
| 2007/0086577 A1 | 4/2007 | Kobayashi |
| 2007/0172020 A1 | 7/2007 | Nambu |
| 2007/0195930 A1 | 8/2007 | Kapatoes |
| 2008/0031406 A1 | 2/2008 | Yan |
| 2008/0049896 A1 | 2/2008 | Kuduvalli |
| 2008/0049898 A1 | 2/2008 | Romesberg, III |
| 2008/0091388 A1 | 4/2008 | Failla |
| 2008/0103834 A1 | 5/2008 | Reiner |
| 2008/0118137 A1 | 5/2008 | Chen |
| 2008/0260368 A1 | 10/2008 | Chang |
| 2008/0292055 A1 | 11/2008 | Boone |
| 2008/0298553 A1 | 12/2008 | Takahashi |
| 2009/0003512 A1 | 1/2009 | Pouliot |
| 2009/0067576 A1 | 3/2009 | Maltz |
| 2009/0090870 A1 | 4/2009 | Ahnesjo |
| 2009/0175418 A1 | 7/2009 | Sakurai |
| 2009/0217999 A1 | 9/2009 | Becker |
| 2009/0227841 A1 | 9/2009 | Miyako |
| 2009/0250618 A1 | 10/2009 | Simon |
| 2009/0252292 A1 | 10/2009 | Simon |
| 2009/0326365 A1 | 12/2009 | Goldenberg |
| 2010/0008467 A1 | 1/2010 | Dussault |
| 2011/0022360 A1 | 1/2011 | Simon |
| 2011/0051893 A1 | 3/2011 | McNutt |
| 2011/0085716 A1 | 4/2011 | Christophe |
| 2011/0096906 A1 | 4/2011 | Langeveld |
| 2011/0158386 A1 | 6/2011 | Payne |
| 2011/0204262 A1 | 8/2011 | Pu |
| 2011/0210258 A1 | 9/2011 | Black |
| 2011/0248188 A1 | 10/2011 | Brusasco |
| 2011/0278444 A1 | 11/2011 | Navarro |
| 2011/0306864 A1 | 12/2011 | Zarate |
| 2012/0014618 A1 | 1/2012 | Sun |
| 2012/0025105 A1 | 2/2012 | Brown |
| 2012/0025826 A1 | 2/2012 | Zhou |
| 2012/0230462 A1 | 9/2012 | Robar |
| 2012/0292517 A1 | 11/2012 | Izaguirre |
| 2012/0305793 A1 | 12/2012 | Schiefer |
| 2012/0326057 A1 | 12/2012 | Remeijer |
| 2013/0048883 A1 | 2/2013 | Simon |
| 2013/0258105 A1 | 10/2013 | Jozsef |
| 2013/0303902 A1 | 11/2013 | Smith |
| 2014/0016754 A1 | 1/2014 | Sugiyama |
| 2014/0064445 A1 | 3/2014 | Adler |
| 2014/0073834 A1* | 3/2014 | Hildreth ............... A61N 5/1048 600/1 |
| 2014/0077098 A1 | 3/2014 | Tachikawa |
| 2014/0094642 A1 | 4/2014 | Fuji |
| 2014/0105355 A1 | 4/2014 | Toimela |
| 2014/0263990 A1 | 9/2014 | Kawrykow |
| 2015/0080634 A1 | 3/2015 | Huber |
| 2015/0087879 A1* | 3/2015 | Nelms .................. A61N 5/103 600/1 |
| 2015/0108356 A1 | 4/2015 | Seuntjens |
| 2015/0124930 A1* | 5/2015 | Verhaegen ........... A61N 5/1047 250/252.1 |
| 2015/0238778 A1 | 8/2015 | Hildreth |
| 2015/0283403 A1 | 10/2015 | Kapatoes |
| 2015/0309193 A1 | 10/2015 | Kozelka |
| 2015/0327825 A1 | 11/2015 | Suzuki |
| 2015/0352376 A1 | 12/2015 | Wiggers |
| 2016/0067479 A1 | 3/2016 | Marcovecchio |
| 2016/0136460 A1 | 5/2016 | Baltes |
| 2016/0166857 A1 | 6/2016 | Nelms |
| 2016/0287906 A1* | 10/2016 | Nord .................... A61N 5/1071 |
| 2016/0310762 A1 | 10/2016 | Ramezanzadeh Moghadam |
| 2017/0021194 A1 | 1/2017 | Nelms |
| 2017/0173367 A1 | 6/2017 | Seuntjens |
| 2017/0177812 A1 | 6/2017 | Sjölund |
| 2017/0225015 A1 | 8/2017 | Thieme |
| 2017/0274225 A1 | 9/2017 | Baecklund |
| 2018/0028143 A1 | 2/2018 | Wiggers |
| 2018/0140272 A1 | 5/2018 | Ruchala |
| 2018/0185672 A1 | 7/2018 | Ramezanzadeh Moghadam |
| 2018/0243586 A1 | 8/2018 | Ramezanzadeh Moghadam et al. |
| 2018/0250529 A1 | 9/2018 | Seuntjens |
| 2018/0250531 A1 | 9/2018 | Ansorge |
| 2019/0298285 A1 | 10/2019 | Rakic |
| 2020/0253001 A1 | 8/2020 | Nauditt |

FOREIGN PATENT DOCUMENTS

| | | |
|---|---|---|
| EP | 1060726 | 12/2000 |
| EP | 1060726 B1 | 6/2004 |
| EP | 2016445 | 1/2009 |
| EP | 2078537 A1 | 7/2009 |
| EP | 2117649 A2 | 11/2009 |
| EP | 2186542 | 5/2010 |
| EP | 2457237 | 5/2012 |
| EP | 2708919 A2 | 3/2014 |
| EP | 2865417 | 4/2015 |
| EP | 2904974 | 8/2015 |
| EP | 3074088 | 10/2016 |
| EP | 3075417 | 10/2016 |
| JP | 05154209 | 6/1993 |
| JP | 2003310590 A | 11/2003 |
| JP | 2008105882 | 5/2008 |
| JP | 2010215428 | 9/2010 |
| JP | 2010234521 | 10/2010 |
| WO | 2006138513 | 12/2006 |
| WO | 2008013956 | 1/2008 |
| WO | 2009114669 | 9/2009 |
| WO | 2009120494 | 10/2009 |
| WO | 2009137794 | 11/2009 |
| WO | 2011011471 | 1/2011 |
| WO | 2012053440 | 4/2012 |
| WO | 2013049839 | 4/2013 |
| WO | 2013177677 A | 12/2013 |
| WO | 2015024360 | 2/2015 |
| WO | 2015073899 | 5/2015 |
| WO | 2016172352 | 10/2016 |
| WO | 2016200463 | 12/2016 |
| WO | 2019157249 A | 8/2019 |

OTHER PUBLICATIONS

"Rapid Arc"; Varian Medical Systems, Inc., Palo Alto, CA; www.varian.com; 2007; pp. 1-8.

"VMAT"; Elekta,Ltd., Crawley UK; Document No. 4513 3710770; Oct. 8, 2008, 8 pages.

"Waterphantom Dosimetry"; Medical Physics, vol. 3, May/Jun. 1976; pp. 189.

Ahnesjo et al., "Calculation and Application of Point Spread Functions for Treatment Planning with High Energy Photon Beams", Acta. Oncol., 26, 49-56, 1987.

Ahnesjo et al., "Dose calculations for external photon beams in radiotherapy", Phys. Med. Biol. 44, R99-R155 1999.

Ahnesjo, "Collapsed Cone Convolution of Radiant Energy for Photon Dose Calculation in Heterogeneous Media", Med. Phys. 16, 577-92, 1989.

Albers et al., CRC HAndbook of Chemistry and Physics, 87th Ed., Edited by R.C. Weast CRC, Cleveland, 1976. pp. F-11, D-171, E-6. (4 pages).

(56) References Cited

OTHER PUBLICATIONS

Almond et al. In "AAPM TG-51 Protocol for Clinical Reference Dosimetry of High Energy Photon and Electron Beams", Med. Phys. VI, 26, pp. 1847-1870, 1999.
Amanatides et al., "A Fast Voxel Traversal Algorithm for Ray Tracing", Eurographics '87, Conference Proceedings, 1987, 10 pages.
Aspen Aerogels, Pyrogel.RTM. 2250 Datasheet (Aspen Aerogels, Inc., Northborough, 2010). 2 pages.
Benedick Fraass; "Quality Assurance for Clinical Radiotherapy Treatment Planning," Med Phys., 25(10), Oct. 1998; pp. 1773-1829.
Berlyand et al., "Portable Calorimeter for Measuring Absorbed Doses of X-Rays and Electrons from Accelerators", translated from Izeritel'naya Teknika, No. 11, Nov. 1991, pp. 56-58.
Boutillon in "Gap Correction for the Calorimetric Measurement of Absorbed Dose in Graphite with a 60Co Beam", Phys. Med. Biol., vol. 34, pp. 1809-1821, 1989.
Brusasco, C, et al. 'A Dosimetry System for Fast Measurement of 3D Depth-dose Profiles in Charged-particle Tumor Therapy with Scanning Techniques.' Nuclear Instruments & Methods In Physics Research, Section-B: Beam Interactions With Materials And Atom 168.4 (2000): 578-92.
Cyberknife; Cyberknife Systems; "The Standard of Radiosurgery", by Accuracy, Sunnyvale, CA; 2009; pp. 1-6.
D.W.O. Rogers; "Montey Carlo Techniques in Radiotherapy," Physics in Canada, Medical Physics Special Issue, v. 58 #2; 2002; pp. 63-70.
Daures et al., "New Constant-Temperature Operating Mode for Graphite Calorimeter at LNE-LNHB", Physics in Medicine and Biology, vol. 50, 2005, No. pp. 4035-4052.
Daures et al., "Small section graphite calorimeter (CR10) at LNE-LNHB for measurement in small beams for IMRT", Metrologica, (Dec. 1, 2011), XP020229547, 5 pages.
Daures et al., "Small Section Graphite Calorimeter (GR-10) at LNE-LNHB for Measurements in Small Beams for IMRT Metrologia", vol. 49, No. 5, 2012, pp. S174-S178.
Domen et al., "A Heat-loss-Compensated Calori meter: Theory, Design, and Performance", Journal of Research of the National Bureau of Standards—A. Physics and Chemistry, vol. 78A, No. 5, Sep.-Oct. 1974, pp. 595-610.
Domen, "Absorbed Dose Water Calorimeter", (Med. Phys., vol. 7, 1980, pp. 157-159).
Duane et al., "An Absorbed Dose Calorimeter for IMRT Dosimetry", Metrologia, vol. 49, No. 5, 2012, pp. S168-S173.
EP2277353 Search Report dated Jul. 21, 2017; 10 pages.
EP2457237 Supplemental European Search Report and Written Opinion dated Mar. 8, 2017; 10 pages.
G.J. Kutcher; "Comprehensive AQ for Radiation Oncology Report;" AAPM Radiation Therapy Committee Task Group 40; Med. Phys., 21; Apr. 1994; pp. 581-618.
Iaea, Trs., "398. Absorbed Dose Determination in External Beam Radiotherapy: An International Code of Practice for Dosimetry based on Standards of Absorbed Dose to Water," Vienna International Atomic Energy Agency (2000). 242 pages.
Indra J. Das, Chee-Wai Cheng, Ronald J. Watt, Anders Ahnesjo, John Gibbons, X. Allen Li, Jessica Lowenstien, Raj K. Mitra, William E. Simon, Timothy C. Zhu; Accelerator Beam Data Commissioning Equiptment and Procedures; Report of the TG-106 of the Therapy Physics Committee of the AAPM; Med. Phys. 35(9), Sep. 2008; pp. 4186-4215.
International Search Report and Written Opinion dated Oct. 2, 2020, PCT Application No. PCT/US2020/041458.
J. Seuntjens and S. Duane, "Photon absorbed dose standards," Metrologia 46, S39-S58 (2009).
Joseph O. Deasy; "A Computational Environment for Radiotherapy Research," Med. Phys. 30, (5), May 2003; pp. 979-985.
Kawrakow et al. In "The EGSnrc Code System: Monte-Carlo Simulation of Electron and Photon Transport" (Canadian National Research Center, NRC Report PIRS-701, 2006.

Linacre, J.K., "Harwell Graphite Calorimeter", IAEA, vol. 47, 1970 (pp. 46-54.).
Liu et al., "Correcting kernel tilting and hardening in convolution/superposition dose calculations for clinical devergent and polychomatic photon beams", Med. Phys. 24, 1729-1741, 1997.
Lu et al., "Accurate convolution/superposition for multi-resolution dose calculation using cumulative tabulated kernels", Phys. Med. Biol. 50, 655-680, 2005.
Mackie et al., "A convolution method of calculating dose for 15-MVxrays", Med. Phys. 12, 188-196, 1985.
Mackie et al., "Generation of Photon Energy Deposition Kernels Using the EGS Monte Carlo Code," 1988, Phys. Med. Biol. 33, pp. 1-20.
Mackie et al., "Photon Beam Dose Computations", Proceedings of the 1996 AAPM Summer School, 1996. 36 pages.
Mackie et al., The Use of Comp. In Rad. Ther., 107-110 1987.
MapCALC; www.sunnuclear.com; manufactured by Sun Nuclear Corp.; Melbourne, FL; 2009, 2 pages.
MapCheck and EPIDose; www.sunnuclear.com; manufactured by Sun Nuclear Corp.; Melbourne,FL; 2010, 8 pages.
Mathilda Van Zijtveld, Maaretn L.P. Dirkxa, Hans C.J. De Boera, and Ben J.M. Heijmen; "3D Dose Reconstruction for Clinical Evaluation of IMRT Pretreatment Verification with an EPID." Radiotherapy and Oncology, 82(2); Feb. 2007; pp. 201-201.
Mc Ewen at al., 'A Portable Calorimeter for Measuring Absorbed Dose in the Radiotherapy Clinic', Physics in Medicine and Biology, vol. 45, No. 12, Dec. 2000, pp. 3675-3691.
McDermott et al.; "Replacing Pretreatment Verification with In Vivo EPID Dosimetry for Prostate IMRT"; International Journal of Radiation: Oncology Biology Physics, Pergamon Press, USA, vol. 67, No. 5, Mar. 28, 2007, pp. 1568-1577, XP022101268, ISSN: 0360-3016, DOI: 10.1016/J.IJROBP.2006.11.047.
McDonald et al., "Portable Tissue Equivalent Calorimeter", Medical Physics, vol. 3, 2, Mar.-Apr. 1976, pp. 80-86.
McEwen et al., "Portable Graphite Calorimeter for Measuring Absorbed Dose in the Radiotherapy Clinic", Standards and Codes of Practice in Medical Radiation Dosimetry,IAEA-CN-96-9P,2002, pp. 115-121.
McEwen et al.; "A portable calorimeter for measuring absorbed dose in radiotherapy clinic"; Dec. 2000; Phys. Med. Biol., vol. 45; pp. 3675-3691.
Miller, "Polystyrene Calorimeter for Electron Beam Dose Measurements", Radiation Physics Chemistry vol. 46, No. 4-6, Aug. 1995, pp. 1243-1246.
Mohan et al., "Energy and angular distributions of photons from medical linear accelerators", Med. Phys. 12, 592-597, 1985.
Myers et al., "Precision Adiabatic Gamma-Ray Calorimeter using Thermistor Thermometry", Review of Scientific Instruments, vol. 32, No. 9, Sep. 1961, pp. 1013-1015.
Nelms, Benjamin et al.; "Evalution of a Fast Method of EPID-based Dosimetry for Intensity-modulated Radiation Therapy"; Journal of Applied Clinical Medical Physics, Jan. 1, 2010, pp. 140-157, XP055476020.
Nelms, Benjamin. "Variation in External Beam Treatment, Plan Quality: An Inter-institutional Study of Planners and Planning Systems." Practical Radiation Oncology 2.4 (2012): 296-305.
Nutbrown et. "Evaluation of Factors to Convert Absorbed Dose Calibrations in Graphite to Water for Mega-Voltage Photon Beams" (UK National Pysical Laboratory, NPL Report CIRM 37, 2000. 45 pages.
Ostrowsky et al., "The Construction of the Graphite Calorimeter GR9 at LNE-LNHB (Geometrical and technical considerations)", Report CEA-R-6184, 2008, 52 pages.
Otto, "Volumetric modulated arc therapy: IMRT in a single gantry arc", Med. Phys. 35, 310-317, 2008.
Owen et al. "Correction for the Effect of the Gaps around the Core of an Absorbed Dose Graphite Calorimeter in High Energy Photon Radiation" (Phys. Med. Biol., vol. 36, pp. 1699-1704, 1991.
Palmans et al., "A Small-Body Portable Graphite Calorimeter for Dosimetry in Low-Energy Clinical Proton Beams", Physics in Medicine and Biology, vol. 49, No. 16, Aug. 2004, pp. 3737-3749.
Papanikolaou et al., "Investigation of the convolution method for polyenergetic spectra", Med. Phys. 20, 1327-1336, 1993.

(56) References Cited

OTHER PUBLICATIONS

PCT App. No. PCT/US2009/036775; International Preliminary Report on Patentability Chapter II and Written Opinion dated Sep. 12, 2010; 12 pages.
PCT App. No. PCT/US2009/036775; International Search Report dated Nov. 12, 2009; 2 pages.
PCT App. No. PCT/US2009/036917; International Preliminary Report on Chapter II Patentability dated Mar. 15, 2011. 3 pages.
PCT App. No. PCT/US2009/036917; International Search Report dated Sep. 17, 2009. 2 pages.
PCT App. No. PCT/US2009/036917; Written Opinion dated Sep. 12, 2010; 4 pages.
PCT App. No. PCT/US2009/043341; International Preliminary Report on Patentability Chapter I dated Nov. 9, 2010. 4 pages.
PCT App. No. PCT/US2009/043341; International Search Report dated Jan. 5, 2010. 3 pages.
PCT App. No. PCT/US2009/043341; Written Opinion of the International Search Authority dated Nov. 8, 2010. 3 pages.
PCT App. No. PCT/US2010/042680; International Preliminary Report on Patentability Chapter I dated Jan. 24, 2012; 9 pages.
PCT App. No. PCT/US2010/042680; International Search Report dated Jan. 27, 2011; 2 pages.
PCT App. No. PCT/US2010/042680; International Written Opinion dated Jan. 23, 2012; 8 pages.
PCT App. No. PCT/US2012/053440; International Preliminary Report on Patentability Chapter I dated Mar. 3, 2015; 8 pages.
PCT App. No. PCT/US2012/053440; International Search Report and Written Opinion dated Mar. 26, 2014; 3 pages.
PCT App. No. PCT/US2012/058345; International Preliminary Report on Patentability Chapter I dated Apr. 1, 2014; 5 pages.
PCT App. No. PCT/US2012/058345; International Search Report dated Apr. 17, 2013; 3 pages.
PCT App. No. PCT/US2012/058345; International Written Opinion of the International Search Authority dated Mar. 29, 2014; 4 pages.
PCT App. No. PCT/US2014/065808; International Preliminary Report on Patentability Chapter I dated May 17, 2016; 7 pages.
PCT App. No. PCT/US2014/065808; International Search Report and Written Opinion dated May 21, 2015; 9 pages.
PCT App. No. PCT/US2015/024360; International Preliminary Report on Patentability Chapter I dated Oct. 4, 2016; 9 pages.
PCT App. No. PCT/US2015/024360; International Search Report and Written Opinion dated Oct. 8, 2015; 13 page.
PCT App. No. PCT/US2016/028664; International Preliminary Report on Patentability dated Nov. 2, 2017; 5 pages.
PCT App. No. PCT/US2017/062608; International Search Report and Written Opinion dated Feb. 22, 2018; 11 pages.
PCT App. No. PCT/US2018/020320; International Preliminary Report on Patentability Chapter I dated Sep. 12, 2019. pp. 1-11.
PCT App. No. PCT/US2018/020320; International Search Report and Written Opinion dated Jul. 24, 2018; 18 pages.
PCT Appl. No. PCT/US2018/056568; International Preliminary Report on Patentability, dated Apr. 30, 2020. 8 pages.
PCT/US2017/044472; International Search Report and Written Opinion of the International Searching Authority, or the Declaration dated Oct. 13, 2017; 12 pages.

Petree et al., "A Comparison of Absorbed Dose Determinations in Graphite by Cavity Ionization Measurements and by Calorimetry", Journal of Research of the National Bureau of Standards—C. Engineering and Instrumentation, vol. 71 C, No. 1, Jan.- Mar. 1967, pp. 19-27.
Picard et al., "Construction of an Absorbed-Dose Graphite Calorimeter", Report BIPM-09/01' May 2009, 12 pages.
R. Alfonso et al., 'A new formalism for reference dosimetry of small and nonstandard fields,' Med. Phys. 35, 5179-5186 (2008).
Renaud et al., "Development of a graphite probe calorimeter for absolute clinical dosimetry", Med. Phvs., (Jan. 9, 2013), vol. 40, No. 2, p. 020701, XP012170941, 6 pages.
Robert M. Eisberg; "Fundamentals of Modern Physics," Chapter 9—Perturbation Theory; John Wiley & Sons; 1967; pp. 268-272.
Rogers, "The physics of AAPM's TG-51 protocol," in Clinical Dosimetry Measurements in Radiotherapy, Medical Physics Monograph No. 34, edited by D. W. O. Rogers and J. E. Cygler (Medical Physics Publishing, Madison, WI, 2009), pp. 239-298.
Ross et al. In "Water Calorimetry for Radiation Dosimetry" (Phys. Med. Biol., 1996, vol. 41, pp. 1-29).
S. Picard, D. T. Burns, and P. Roger, "Determination of the specific heat capacity of a graphite sample using absolute and differential methods," Metrologia 44, 294-302 (2007).
Sander et al., "NPL's new absorbed dose standard for the calibration of HDR 192Ir brachytherapy sources," Metrologia 49, S184-S188 (2012).
Seuntjens et al., Review of Calorimeter Based Absorbed Dose to Water Standards, Standards and Codes of Practice in Medical Radiation Dosimetry, IAEA-CN-96-3, 2002 p. 37-66.
Stewart in "The Development of New Devices for Accurate Radiation Dose Measurement: A garded Liquid Ionization Chamber and an Electron Sealed Water Calorimeter" Ph. D. Dissertation McGill University, 2007.
Sundara et al., "Graphite Calorimeter in Water and Calibration of Ionization Chambers in Dose to Water for 60Co Gamma Radiation", Medical Physics, vol. 7, No. 3, May-Jun. 1980, pp. 196-201.
T.R. McNutt, T.R. Mackie, P.J. Reckwerdt, B.R. Paliwal; "Analysis and Convergence of the Iterative Convolution/Superposition Dose Reconstruction Technique,"; Med. Phys. 24(9) Sep. 1997; pp. 1465-1476.
Williams, "Pyramidal Parametrics", SIGGRAPH Comput. Graph. 17, 3, 1-11, 1983.
Witzani et al., "A Graphite Absorbed-Dose Calorimeter in the Quasi-Isothermal Mode of Operation", Metrologia, vol. 20, No. 3, 1984, pp. 73-79.
Y. Morishita et al., "A standard for absorbed dose rate to water in a 60Co field using a graphite calorimeter at the national metrology institute of Japan," Radiat. Prot. Dosim. 1-9 (2012) (published E-first Sep. 5, 2012).
Yan et al., "Adaptive radiation therapy", Phys. Med. Biol. 42, 123-132, 1997.
Yu, "Intensity-modulated arc therapy with dynamic multileaf collimation: an alternative to tomotherapy", Phys. Med. Biol. 40, 1435-1449, 1995.
International Search Report and Written Opinion dated Nov. 24, 2021, PCT Application No. PCT/IB2021/057573.

\* cited by examiner

RADIATION DETECTOR CALIBRATION

RELATED APPLICATION(S)

This application is a continuation of and claims priority to and the benefit of U.S. application Ser. No. 16/846,227, filed Apr. 10, 2020, which is a continuation of U.S. application Ser. No. 14/694,865, filed Apr. 23, 2015, titled "Radiation Detector Calibration," the contents of each are is hereby incorporated by reference.

TECHNICAL FIELD

Radiation therapy quality assurance utilizing radiation detectors.

BACKGROUND

Radiation therapy is used to treat cancerous tumors with ionizing radiation that kills the affected cancer cells. External beam radiotherapy is one method for delivering the ionizing radiation. In such therapy, a patient is placed on a couch and a radiotherapy beam generator (for example, a linear accelerator) is positioned to direct the ionizing radiation at the patient's tumor. One method for determining the proper positioning of the patient with respect to the beam is to use data from a radiation detector, for example an electronic portal imaging device (EPID). Images from an EPID depict the radiation exiting the patient, essentially providing an x-ray image that can be used to properly locate the patient with respect to the beam. Some modern EPID devices use a phosphor and an array of photosensors to detect radiation exiting the patient. Light from the phosphor is converted to an electrical signal and read by a computer to generate a mapping of the radiation pattern striking the phosphor.

SUMMARY

In one aspect, a radiation treatment plan and patient anatomy information is received. During delivery of patient treatment, exit radiation measurement information is acquired by a radiation detector. Utilizing at least the exit radiation measurement information, the patient anatomy information and at least a portion of the radiation treatment plan, a radiation detector response calibration is determined.

In some variations one or more of the following features can optionally be included in any feasible combination.

In one interrelated aspect, determining the radiation detector response calibration can further include determining a patient entrance fluence during a period of time when the exit radiation measurement information was acquired. Utilizing the patient entrance fluence and the patient anatomy information, the patient exit fluence can be determined. The patient exit fluence can be associated with at least a portion of the exit radiation measurement information to arrive at the radiation detector response calibration.

In another interrelated aspect, associating the patient exit fluence with the exit radiation measurement information can further include analyzing the heterogeneities inside the patient, and at least part of the radiation plan, to find a subset of the exit radiation measurement information for creating a list of suitable points to be used for arriving at the radiation detector response calibration. A grouping can be formed from the list of suitable points to arrive at a radiation detector response calibration for each grouping.

In yet another interrelated aspect, the operations determining the patient entrance fluence can also include determining an image start time and an image end time, where the image start time and image end time define the period of time when an image was acquired. The patient entrance fluence can be determined utilizing the at least a portion of the radiation treatment plan and the image start time and image end time.

In another interrelated aspect, the operations determining the image start time and the image end time can include determining estimated collimator profiles from at least a portion of the radiation treatment plan. The estimated collimator profiles can be compared to a measured collimator profile acquired by the radiation detector. The image start time and image end time can be determined from the best match between the estimated collimator profiles and the measured collimator profile.

In a further interrelated aspect, a difference between the measured collimator profile and the best matched estimated collimator profile can be determined. In an effort to arrive at a more accurate image start time and image end time, a range of possible times for the image start time and the image end time used to determine the estimated collimator profiles can be increased if the difference exceeds a predetermined value.

In yet another interrelated aspect, the radiation detector can be an electronic portal imaging device.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a computer-readable storage medium, may include, encode, store or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings and from the claims. While certain features of the currently disclosed subject matter are described for illustrative purposes, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features or elements.

DETAILED DESCRIPTION

The current subject matter is directed to methods, systems, software and apparatus for calibrating a radiation detector. A radiation detector can detect radiation from a radiation therapy device as it exits a patient. This can be used for positioning the patient, but also for radiation therapy quality assurance.

If an accurate calibration of a radiation detector device is available, radiation detector output can be converted to an estimation of dose, and used for radiation therapy quality assurance. As used herein, the term "dose" can refer to any radiation measurement quantity, or combination of quantities, which provide an estimate of the dose or fluence. When a radiation detector is able to measure the radiation that has been transmitted through a patient during treatment, this information can be used with patient anatomy information to determine whether the radiation treatment plan was delivered as intended.

One exemplary embodiment described herein relates to the radiation detector being an EPID device, however, the radiation detector can be any type of radiation detector. For example, the radiation detector could be a device that directly uses diodes without a phosphor.

Figure 1:
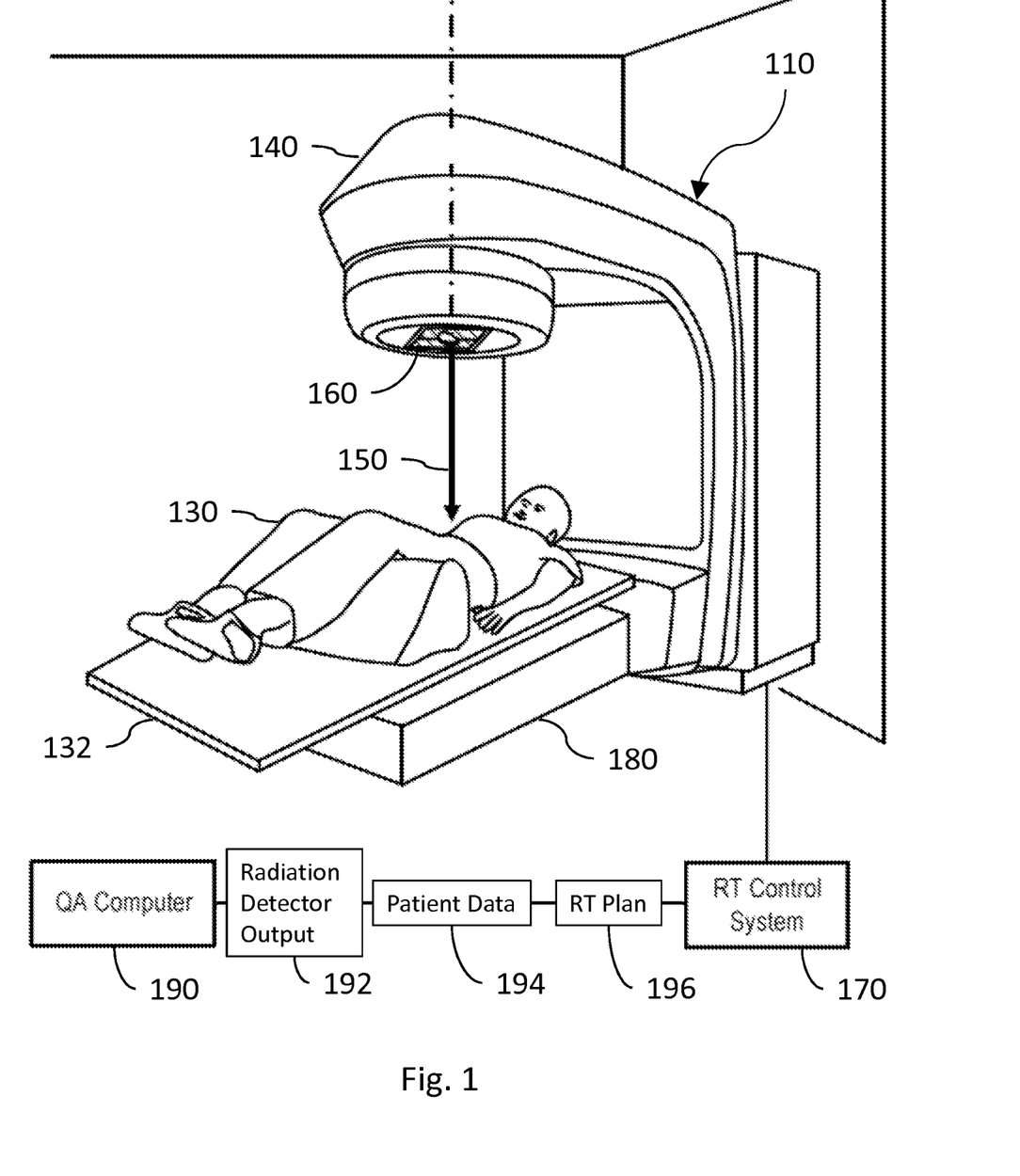
FIG. 1 is a simplified diagram illustrating a radiation therapy device equipped with a radiation detector for measuring radiation exiting from a patient.

FIG. 1 illustrates an exemplary radiation therapy device 110 equipped with a radiation detector 180 for measuring the radiation exiting from a patient 130. The radiation therapy device 110 can include a gantry 140 that can rotate about the patient 130. Inside gantry 140, there is a radiation source, for example, a linear accelerator (LINAC), cobalt 60 source, etc., that directs radiation toward patient 130 in the form of treatment beam 150. The treatment beam 150 can also include scanning beams, where a small beamlet is scanned over the area that is required to be treated. The treatment beam 150 may be shaped by a collimator 160, for example, a multi-leaf collimator (MLC), before reaching patient 130. In the example of the collimator 160 being a MLC, the collimation may block part of treatment beam 150 by providing a series of narrow gaps between opposite leaves of the MLC, which combine across multiple leaf pairs to form a desired shape, typically similar to the tumor that is being irradiated. The example of a multi-leaf collimator is used herein; however present disclosure contemplates any type of collimation device.

The treatment of patient 130 can be controlled by a radiation therapy control system 170, which can include, for example, processors, computers, hardware, computer programs, etc., that control the administration of a radiation treatment plan 196 for the patient 130. The radiation therapy control system 170 can control, for example, treatment beam 150, position of gantry 140, beam shape created by collimators 160, etc.

Radiation treatment plans, as used herein, can include any type of information about radiation delivery, such as a treatment plan, obtained in any manner, for example, delivery log information, or any measurements or other data that can provide information about the patient entrance fluence, etc. Typical radiation treatment plans further involve defining specific machine parameters at precise, and typically fine, time intervals to most closely deliver the specified dose of radiation to the target volume in the patient 130. Common parameters used in radiation treatment plans can include, for example, treatment beam shape or energy, orientation of the gantry, collimator leaf positions, patient anatomy (CT) image orientation with respect to the treatment beam, etc.

The patient 130 can rest on patient couch 132 during treatment. After radiation passes through patient 130 and, at times, patient couch 132, the radiation can impact radiation detector 180. In most implementations, radiation detector 180 is connected to gantry 140 or otherwise made to rotate with gantry 140.

Radiation impacting the radiation detector 180 may be detected as a pattern related to the transmission and absorption of the radiation by the patient anatomy and/or tumor(s). Radiation detector 180 may convert the incident radiation to other wavelengths of light, via a phosphor layer (not shown) in radiation detector 180. Light from the phosphor may then be detected by photosensors (not shown) and converted into an electrical signal, essentially creating a pixel map for the radiation incident on radiation detector 180. The electrical signals from radiation detector 180 can be acquired by, for example, analog-to-digital convertors, digitizers, etc. to acquire, filter, analyze, store or otherwise process the acquired exit radiation measurement information.

As part of the monitoring and quality assurance of radiotherapy treatment, systems and diagnostics can be used to estimate the dose delivered to the patient 130 and compare it to the goals specified by the radiation treatment plan. Such systems or software can be integrated into the radiotherapy control system or may be part of a separate quality assurance (QA) computer 190 (as shown in FIG. 1). While the embodiment described herein utilizes a separate quality assurance computer, the present disclosure contemplates the concepts disclosed herein being implemented within the radiation therapy device's control system or any other related system. Though FIG. 1 shows the QA computer 190 and the radiation therapy control system 170 as separate components, the functionality described herein can be performed on an integrated system or distributed across any number or type of hardware or software components that enable the specified functions herein to be performed.

In one implementation, there can be a radiation detector calibration program (not shown) that performs calibration of radiation detector 180 as described herein. The radiation detector can be executed by a QA computer 190, with a radiation therapy control system 170 or on any other computer or processor connected to radiation therapy device 110. In other implementations, the radiation detector calibration program can be stored and/or executed on an independent computer. The data that the radiation detector calibration program requires to perform the radiation detector calibration, for example, radiation detector output 192, patient data 194, a radiation treatment plan 196, etc. can be received by the radiation detector calibration program and executed on the computer running the radiation detector calibration program. The output of the radiation detector calibration program can be loaded and/or stored onto any connected computing system. The connections between any of the systems described herein can be wired, wireless or any combination thereof.

Figure 2:
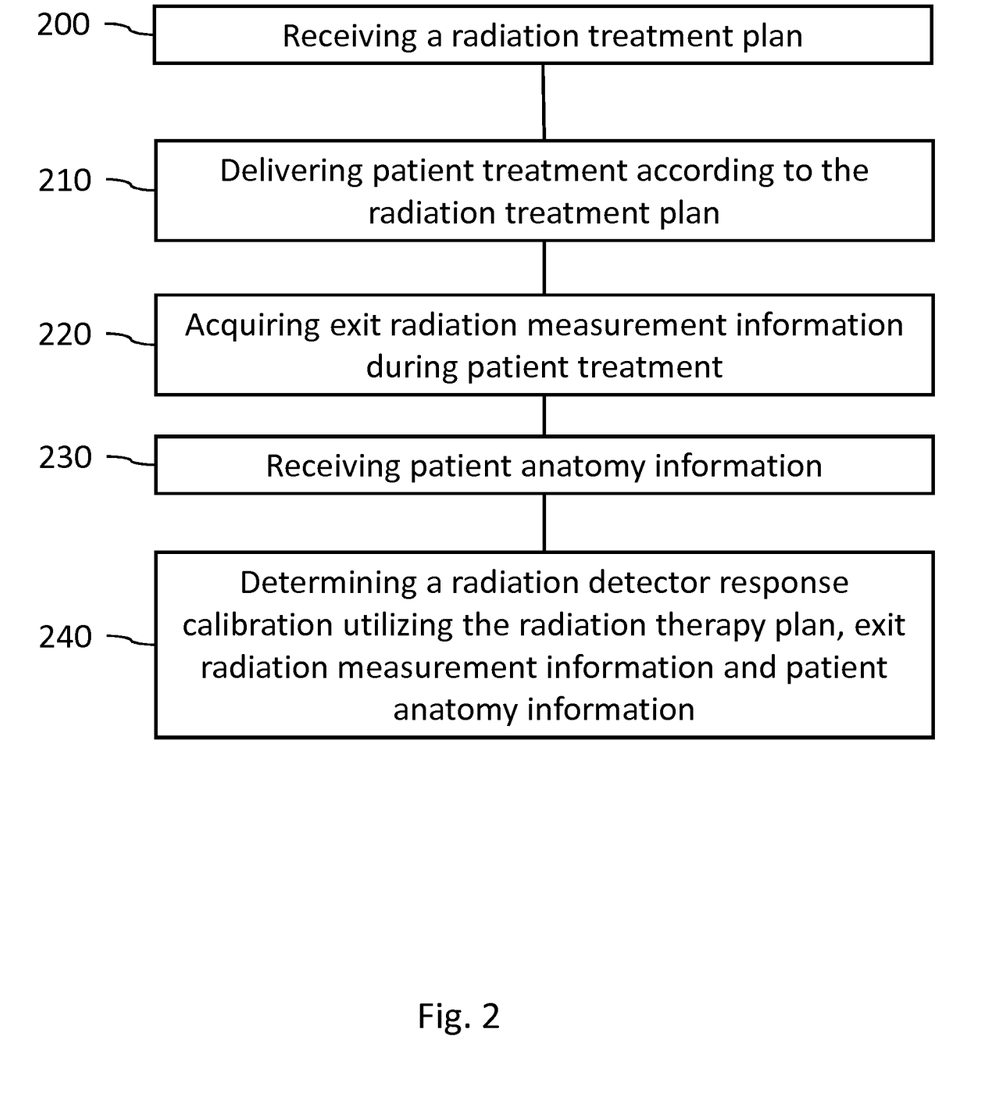
FIG. 2 is a process flow diagram illustrating an exemplary process for the determination of a radiation detector response calibration based on exit radiation measurement information, patient anatomy information and a portion of a radiation treatment plan.

FIG. 2 is a process flow diagram illustrating an exemplary process for determination of a radiation detector response calibration based on exit radiation measurement information, patient anatomy information and at least a portion of a radiation treatment plan. At 200, a radiation treatment plan can be received. At 210, patient treatment can be delivered according to radiation treatment plan 196. At 220, during patient treatment, exit radiation measurement information can be acquired that characterizes the radiation striking radiation detector 180. At 230, patient anatomy information 194 can be received that details the physiological structure of patient 130. Patient anatomy information 194 can include CAT scans, MRI scans, CT scans, radiotherapy structure sets with density overrides, or any other types of patient anatomy information. Patient anatomy information 194 may be acquired before, during or after treatment. At 240, a radiation detector response calibration can be determined utilizing at least a portion of radiation treatment plan 196, treatment delivery logs, measured entrance fluence that was measured before, during, or after the treatment, or the exit radiation measurement information and the patient anatomy information 194.

The radiation detector response calibration can convert the output of the radiation detector, such as an EPID, to a quantity useful for quality assurance purposes such as fluence, dose received by the radiation detector, etc. In one implementation, the radiation detector response calibration can relate the measured signal of the radiation detector to a calculated dose to the patient based on patient anatomy information 194 and at least a portion of the radiation treatment plan 196. The radiation detector response calibration can also be used in order to calculate an expected or predicted exit dose/fluence image for a patient using the radiation treatment plan and the patient anatomy information. The radiation treatment plan and patient anatomy information can serve as a baseline to compare against the measurements acquired during the actual treatment delivery for the purpose of verifying the quality of the treatment delivery to the patient.

Any of the information or data described herein can be received by and/or processed on, for example, QA computer 190, radiation therapy control system 170, other connected or networked computing systems, etc. Similarly, the radiation detector response calibration can be computed, processed or stored by or on any combination of connected computing systems.

The present disclosure's capability of performing radiation detector calibration on an ongoing basis, for example, during patient treatments, relieves the practitioner from dedicating downtime for the radiation therapy device in order to calibrate the device with a phantom. While the present implementation relieves the practitioner of the need to use phantoms, should it be desired to perform the calibration with a phantom, an anthropomorphic or other heterogeneous phantom, non-spherical homogenous phantoms, or homogenous spherically symmetric phantoms placed asymmetrically with respect to the machine isocenter on the treatment couch, the calibration method described herein can be applied in such a manner.

Figure 3:
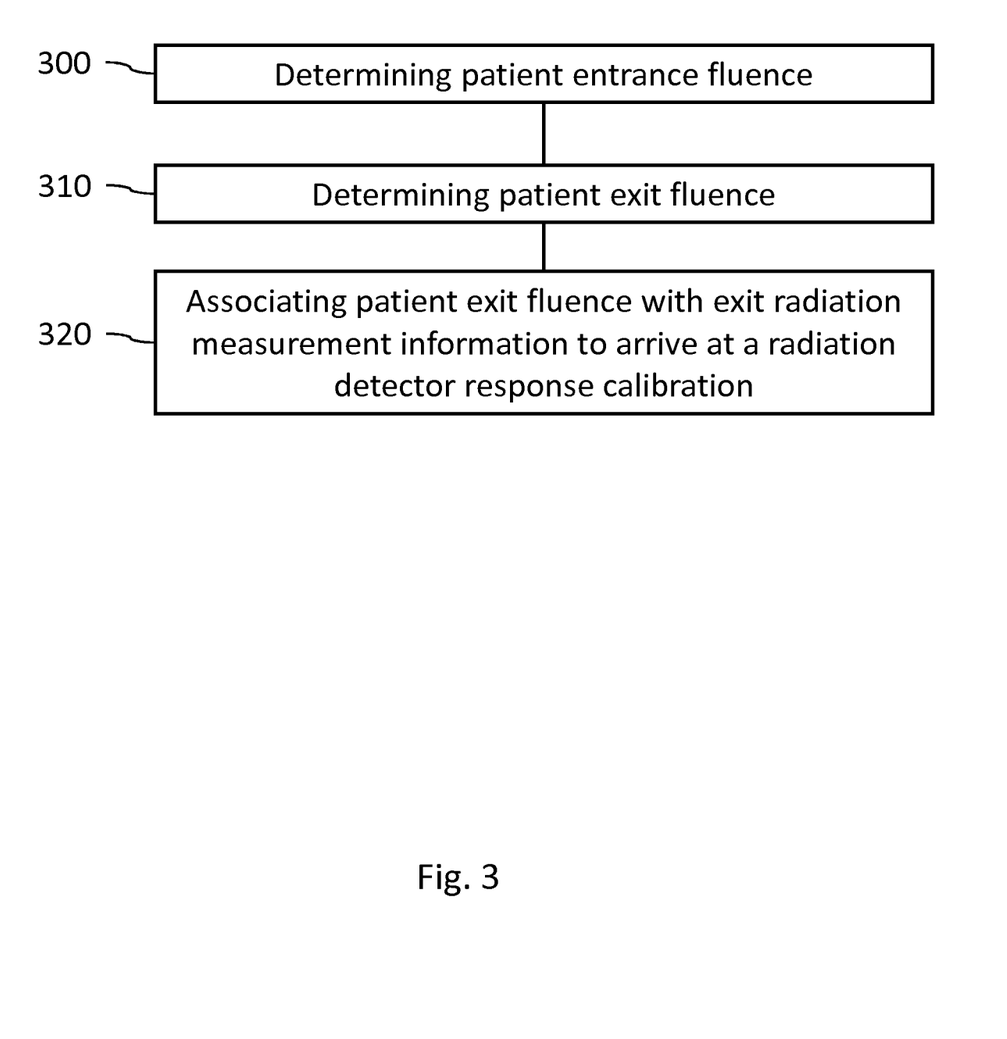
FIG. 3 is a process flow diagram illustrating an exemplary process for determining a radiation detector response calibration utilizing patient exit fluence and exit radiation measurement information.

FIG. 3 is a process flow diagram further illustrating an exemplary process for determining a radiation detector response calibration. In discussing a particular embodiment, the present disclosure refers to "images," "start image," and "end image." Such terms are not intended to limit the types of radiation detectors contemplated to those providing images. Use of these terms contemplates that such includes any type of radiation detector output, for example, data sets or other output that can be expressed as a visual image or any other representation of the radiation detected at the radiation detector. At 300, patient entrance fluence, during the period of time when an image was acquired, can be determined. The determination of patient entrance fluence can be, for example, based on dosimeter measurements, beam profile/output monitor measurements, gantry position measurements, collimator position measurements, the radiation treatment plan 196, other entrance fluence/dose measurement devices, etc. At 310, patient exit fluence, or the dose received by each pixel of the radiation detector, can be calculated utilizing the patient entrance fluence and patient anatomy information 194, for example, by using simple approximations such as TERMA calculations or with more accurate dose calculation algorithms such as convolution superposition, Monte Carlo or linear Boltzmann transport equation solvers, artificial neural networks, or the like. Patient exit fluence can further be dose to the radiation detector, scattered radiation measurements, or any other approximation of radiation exiting the patient. For example, the patient exit fluence can include the fluence exiting the patient 130 after the impinging radiation is absorbed and/or scattered by the physical structure of the patient 130. At 320, the patient exit fluence can be associated with at least a portion of the exit radiation measurement information to arrive at a radiation detector response calibration.

In another implementation of the present disclosure, associating the patient exit fluence with a portion of the exit radiation measurement information can also include analysis of the heterogeneities inside the patient, and at least part of the radiation plan, to find a subset of the exit radiation measurement information for creating a list of suitable points to be used for arriving at the radiation detector response calibration. Using the suitable points, at least one grouping can be formed to arrive at a radiation detector response calibration for each grouping.

In one implementation of the present disclosure, determination of the patient entrance fluence during the time when the image was acquired is aided by finding the image start time and image end time. When these times are known, the patient entrance fluence may be determined through examination of the radiation treatment plan (e.g., beam intensities, collimator positions, etc.) at that same time.

While "times" are discussed herein, it should be understood that such may refer to typical chronological times (e.g., minutes or seconds), gantry angles, control points, delivered radiation, MLC positions, or any other parameter that may define when radiation detector data, or an EPID image, is acquired. For example, radiation treatment plans often describe the manner in which a radiation therapy device delivers treatment in terms of "control points." A control point can be a collection of data points that define the status of the system including, for example, amount of radiation to be delivered, beam energy, collimator positions, gantry angle, gantry rotation direction, patient support position, etc.

Figure 4:
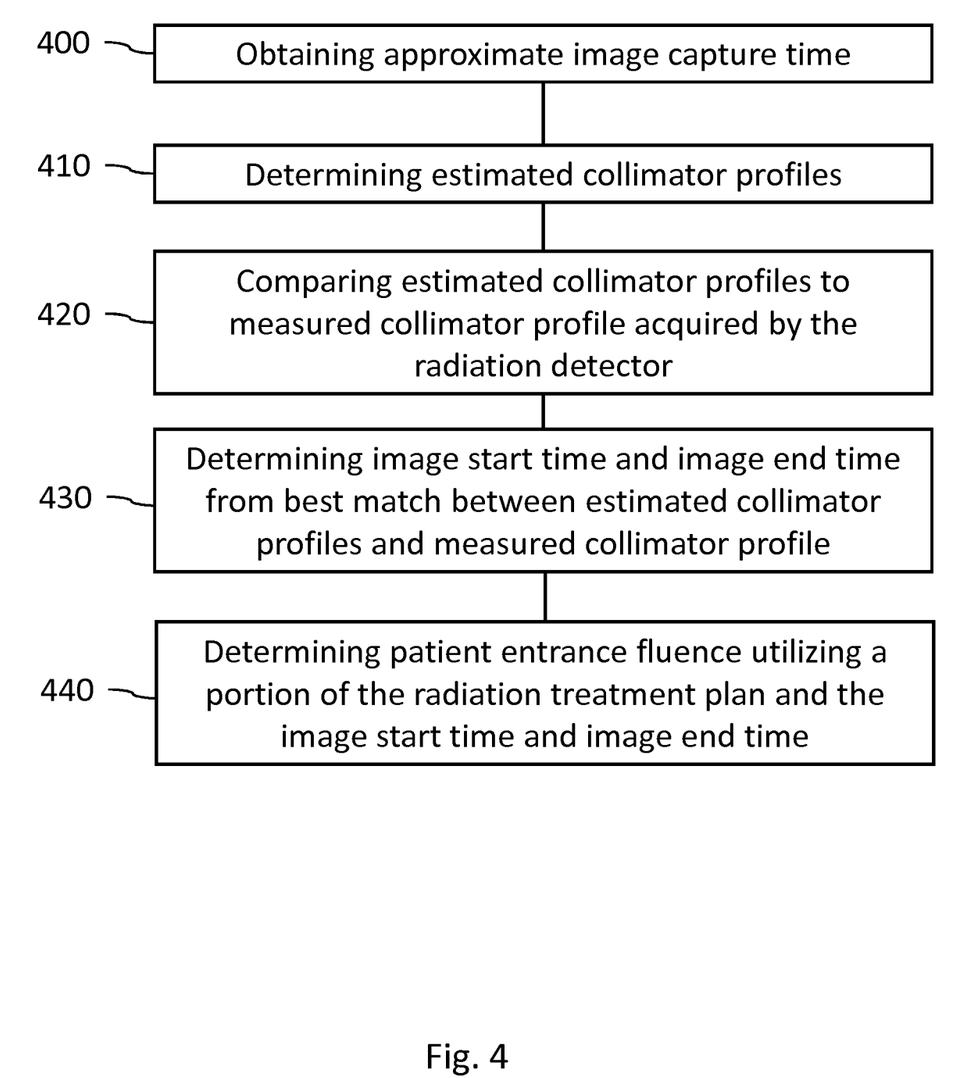
FIG. 4 is a process flow diagram illustrating an exemplary process for determining patient entrance fluence.

FIG. 4 is a process flow diagram illustrating the exemplary process for determining the patient entrance fluence used in the process of FIG. 3. At 400, an approximate image capture time may be obtained, for example, from gantry angle information or the meter-set exposure values in DICOM tags of the EPID frames themselves. At 410, estimated collimator profiles are determined from at least a portion of the radiation treatment plan. These estimated collimator profiles represent the profile expected to be rendered by the radiation detector given an estimated image start time and image end time and the radiation treatment plan characteristics during that time period. At 420, estimated collimator profiles are compared to the actual measured collimator profile that was acquired by the radiation detector. In this comparison, it is not necessary to compare the entire profiles, for example, MLC profiles may be defined as an outline or boundary of the aperture formed by the leaves of the MLC. At 430, the image start time and image end time may be determined from the best match between the estimated collimator profiles and the measured collimator profile. In one implementation, estimated or measured collimator profiles can be also be derived from predicted radiation detector or EPID images.

At 440, patient entrance fluence may be determined by utilizing a portion of the radiation treatment plan and the image start time and image end time. For example, when the actual image start time and image end time are known, the relevant beam characteristics from that period of time (e.g., shape, dose rates, etc.) may be used to calculate the patient entrance fluence during the time when the radiation detector image was acquired.

Figure 5:
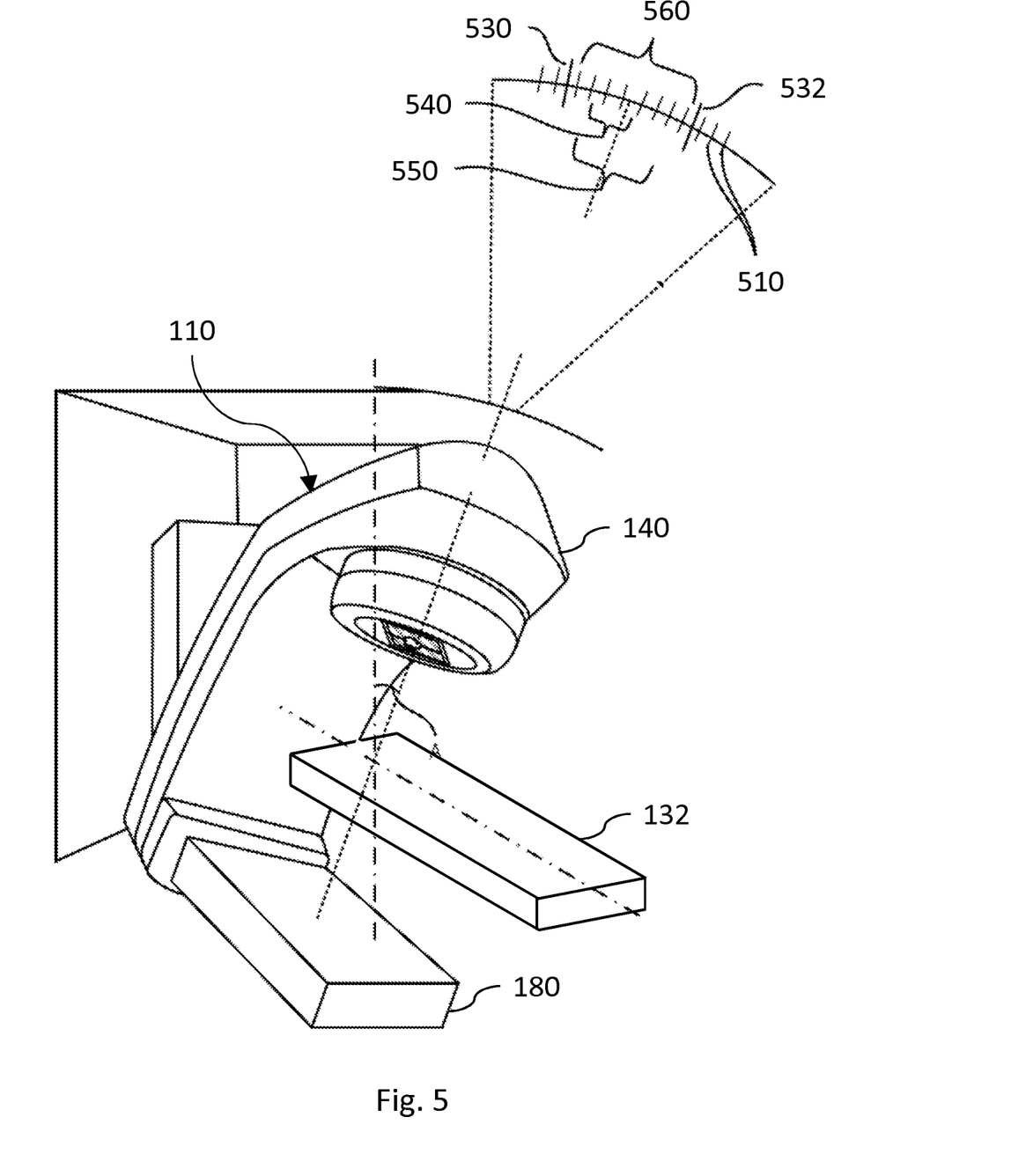
FIG. 5 is a diagram illustrating an exemplary manner of searching for pairs of control points that may provide an image start time and image end time.

FIG. 5 is a diagram illustrating an exemplary manner of searching for the image start time and image end time that produce a best match between an estimated collimator profile and the measured collimator profile that was acquired by the radiation detector. In one implementation, as illustrated in FIG. 5, the initial, approximate image capture time (e.g., from an EPID image's DICOM tag) is represented by angle A of gantry 140. In the example shown, control points 510 are illustrated as angle measures on an expanded view of the gantry rotation arc. The initial, approximate gantry angle A is shown by the central dashed line. The actual image start time 530 and actual image end time 532 are not known a priori, but are shown by the larger lines in the figure. Illustrating the iterative method of the current example, a first pairing of the approximate image start time and the approximate image end time is shown by the bracket 540. Upon comparing the estimated collimator profile for the period denoted by 540 to the measured collimator profile, the fit can be found to be rather poor. The searching algorithm can then determine a second pairing 550 of the approximate image start time and the approximate image end time. Again, the estimated collimator profile can be compared to the measured collimator profile, and the fit can be found to be improved over the first pairing. Similarly, a third pairing 560 can made that can be found to result in a best match between the estimated collimator profile and the measured collimator profile. The determination of the best match can be performed by iterative methods, multi-parameter error minimization, image recognition, distance minimization (between overlapping boundaries), etc.

In another aspect of the present disclosure, the system may calculate a difference between the measured collimator profile and the best matched estimated collimator profile. The difference can be represented by a convergence parameter, error value or any other metric that quantifies the comparison between the measured collimator profile and the estimated collimator profile. If the difference exceeds a predetermined value, a range of possible times for the image start time and the image end time used to calculate the estimated collimator profiles can be increased in an effort to arrive at a more accurate image start time and image end time. For example, if a large difference was due to a bad approximation of the endpoints of the initial search region, such an increase may be needed.

In another implementation there may be a common time base shared between radiation detector 180 and the radiation therapy control system 170. In yet another implementation, there may be a time base (in seconds) corresponding only to the control points 410 and the control point time base (in seconds) and a time base (also in seconds) can be synchronized, interpolated, etc. to obtain a best match between exit radiation measurement information for each image and the control point pairs. In a further implementation, the acquisition of images can be directly tied to coincide with control points 410. For example, when the radiation treatment plan 196 gets to a first starting control point, the radiation detector 180 begins acquiring data, continuing until a second ending control point is reached, at which time the radiation detector 180 stops acquiring data. In this way, the control points 410 can exactly define the image start time 430 and image end time 432. In another implementation especially useful for static collimator and gantry plans, the meter-set exposure, or any other measure of the amount of received radiation or duration of the acquisition, can be used to find the approximate starting and ending time of the radiation detector acquisition.

By comparing the calculated patient exit fluence based on the radiation detector signal, for example, the current or voltage detected at a given pixel of an EPID, to the patient exit fluence computed according to radiation treatment plan as described above, a calibrated radiation detector 180 can indicate a possible error in the delivery of radiation to the patient.

The radiation detector response calibration can include calibration data taken across many types of radiation treatment plans, patient anatomies, etc. A radiation detector response calibration may be expressed as a set of data points for each pixel of a radiation detector 180. A radiation detector response calibration can be built up over time to provide practitioners with calibration data, which can continue to statistically improve as more data is taken during calibrations. For a particular subset of radiation detector response calibration data, a radiation detector response calibration may be expressed as a radiation detector response calibration curve fit through selected data points. A wide variety of fitting methods and functions can be used for obtaining the fitted curve. Also, artificial neural networks can also be used to learn the calibration procedure or to fit the data.

The data points can be based on any of the parameters listed above and can also include pixel response data from the neighboring pixels if needed to improve statistics or take into account overlapping charge distribution or light diffusion through the phosphor. However, different pixels can be impacted at different angles of incidence by different spectra of radiation exiting the patient 130, which, among other things, alters the response of the pixels at different regions of the radiation detector. Therefore, not all data points from all pixels should be used to improve the statistics. Data points can also be grouped according to a particular time range, patient, plan type, treatment site, etc. Data points can be further grouped by, for example, field size, shape, patient distance from the radiation source, patient surface distance from the radiation detector, etc. A separate radiation detector response calibration curve can be obtained for each of these groups or a combination of these groups.

It is understood that the methods of the present disclosure may be utilized with many different types of radiation therapy plans such as arc-based, static field, etc. Moreover, implementations of the current subject matter can provide advantages such as automatic and ongoing calibration of radiation detectors as patients are treated, avoiding calibration drift through the use of continually updated calibration data. In addition, radiation detector calibration for dose may be determined during patient treatment, without the need for phantom calibration.

One or more aspects or features of the subject matter described herein can be realized in digital electronic circuitry, integrated circuitry, specially designed application specific integrated circuits (ASICs), field programmable gate arrays (FPGAs) computer hardware, artificial neural networks, firmware, software and/or combinations thereof. These various aspects or features can include implementation in one or more computer programs that are executable and/or interpretable on a programmable system including at least one programmable processor, which can be special or general purpose, coupled to receive data and instructions from and to transmit data and instructions to, a storage system, at least one input device and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components or code, include machine instructions for a programmable processor and can be implemented in a high-level procedural language, an object-oriented programming language, a functional programming language, a logical programming language and/or in assembly/machine language. As used herein, the term "machine-readable medium" refers to any computer program product, apparatus and/or device, such as for example magnetic discs, optical disks, memory and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback or tactile feedback; and input from the user may be received in any form, including, but not limited to, acoustic, speech or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone or A and B together." A similar interpretation is also intended for lists including three or more items. For example, the phrases "at least one of A, B and C;" "one or more of A, B and C;" and "A, B and/or C" are each intended to mean "A alone, B alone, C alone, A and B together, A and C together, B and C together or A and B and C together." Use of the term "based on," above and in the claims is intended to mean, "based at least in part on," such that an unrecited feature or element is also permissible.

The subject matter described herein can be embodied in systems, apparatus, methods and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown or sequential order, to achieve desirable results. Other implementations may be within the scope of the following claims.

What is claimed is:

1. A system comprising:
   at least one programmable processor; and
   a non-transitory machine-readable medium storing instructions which, when executed by the at least one programmable processor, cause the at least one programmable processor to perform operations comprising:
   receiving at least a portion of a radiation treatment plan;
   deriving a measured collimator profile from exit radiation measurement information acquired with a radiation detector during delivery of patient treatment;
   determining at least one estimated collimator profile from at least a portion of the radiation treatment plan and an approximate image start time and an approximate image end time; and comparing the measured collimator profile with at least one estimated collimator profile to determine an image start time and an image end time.

2. The system of claim 1, wherein the radiation detector is an EPID.

3. The system of claim 1, wherein the measured collimator profile and/or the estimated collimator profile comprise a boundary of an aperture formed by leaves of the collimator.

4. The system of claim 1, the at least one programmable processor further configured to perform operations comprising determining the start and end times by at least determining a best match between the measured collimator profile and more than one estimated collimator profile to determine a best matched collimator profile.

5. The system of claim 4, the at least one programmable processor further configured to perform operations comprising determining the best match by at least minimizing the distance between boundaries of the estimated collimator profile and the measured collimator profile.

6. The system of claim 4, the at least one programmable processor further configured to perform operations comprising:

calculating a difference between the measured collimator profile and the best matched collimator profile; and increasing, in response to the difference exceeding a predetermined value, a range of times for the image start time and the image end time used to calculate the more than one estimated collimator profiles.

7. The system of claim 1, wherein the image start time and image end time correspond to times from the radiation treatment plan.

8. The system of claim 1, the at least one programmable processor further configured to perform operations comprising determining a patient entrance fluence utilizing the portion of the radiation treatment plan and the image start time and image end time.

9. A computer program product comprising a non-transitory, machine-readable medium storing instructions which, when executed by at least one programmable processor, cause the at least one programmable processor to perform operations comprising:

receiving at least a portion of a radiation treatment plan;

deriving a measured collimator profile from exit radiation measurement information acquired with a radiation detector during delivery of patient treatment;

determining at least one estimated collimator profile from at least a portion of the radiation treatment plan and an approximate image start time and an approximate image end time; and comparing the measured collimator profile with at least one estimated collimator profile to determine an image start time and an image end time.

10. The computer program product of claim 9, wherein the radiation detector is an EPID.

11. The computer program product of claim 9, wherein the measured collimator profile and/or the estimated collimator profile comprise a boundary of an aperture formed by leaves of the collimator.

12. The computer program product of claim 9, the operations further comprising determining the start and end times by at least determining a best match between the measured collimator profile and more than one estimated collimator profile to determine a best matched collimator profile.

13. The computer program product of claim 12, the operations further comprising determining the best match by at least minimizing the distance between boundaries of the estimated collimator profile and the measured collimator profile.

14. The computer program product of claim 12, the operations further comprising:

calculating a difference between the measured collimator profile and the best matched collimator profile; and increasing, in response to the difference exceeding a predetermined value, a range of times for the image start time and the image end time used to calculate the more than one estimated collimator profiles.

15. The computer program product of claim 9, wherein the image start time and image end time correspond to times from the radiation treatment plan.

16. The computer program product of claim 9, the at least one programmable processor further configured to perform operations comprising determining a patient entrance fluence utilizing the portion of the radiation treatment plan and the image start time and image end time.

* * * * *